United States Patent

Kimura

Patent Number: 5,844,239
Date of Patent: Dec. 1, 1998

[54] OPTICAL MEASURING APPARATUS FOR LIGHT SCATTERING

[75] Inventor: Eiichi Kimura, Osaka, Japan

[73] Assignees: Kurashiki Boseki Kabushiki Kaisha, Kurashiki; Kyoto Daiichi Kagaku Co., Ltd., Kyoto, both of Japan

[21] Appl. No.: 858,567

[22] Filed: May 19, 1997

[30] Foreign Application Priority Data

May 31, 1996 [JP] Japan .................................. 8-160860

[51] Int. Cl.⁶ .................................................. G01N 21/47
[52] U.S. Cl. .................................. 250/341.8; 250/341.2; 250/349
[58] Field of Search .......................... 250/341.8, 339.07, 250/339.08, 339.1, 339.11, 341.1, 341.2, 341.7, 349

[56] References Cited

U.S. PATENT DOCUMENTS 5,596,992  1/1997  Haaland et al. ................... 250/339.11

FOREIGN PATENT DOCUMENTS 0 627 619  12/1994  European Pat. Off. .
2 361 873   6/1974  Germany .
2 115 175   9/1983  United Kingdom .
2 304 187   3/1997  United Kingdom .
96/41566   12/1996  WIPO .

*Primary Examiner*—Edward J. Glick
*Assistant Examiner*—Darren M. Jiron
*Attorney, Agent, or Firm*—Nikaido, Marmelstein, Murray & Oram LLP

[57] ABSTRACT

Light of a specific wavelength is introduced into respective optical fiber members forming a light projecting optical fiber member group (14a) through a condensing lens (26). A second end of an optical fiber light guide path (10) whose first end is brought into close contact with a target (20) is branched into three optical fiber member groups including a light projecting optical fiber member group (14a) and first and second photoreceiving optical fiber member groups (16a, 18a), and each of the optical fiber member groups (14a, 16a, 18a) is formed by bundling optical fiber members forming respective unit bundles respectively. Each unit bundle includes at least one light projecting optical fiber member which is arranged at the center, a first photoreceiving optical fiber member group arranged around the light projecting optical fiber member substantially on the circumference of a first circle concentric with the optical fiber member, and a second photoreceiving optical fiber member group arranged substantially on the circumference of a second circle which is concentric with the at least one optical fiber member and larger in radius than the first circle.

6 Claims, 9 Drawing Sheets

○ LIGHT PROJECTING FIBER MEMBER
⊘ PHOTORECEIVING FIBER MEMBER GROUP 1
⊛ PHOTORECEIVING FIBER MEMBER GROUP 2

◐ LIGHT PROJECTING FIBER MEMBER
◉ PHOTORECEIVING FIBER MEMBER GROUP 1
✿ PHOTORECEIVING FIBER MEMBER GROUP 2

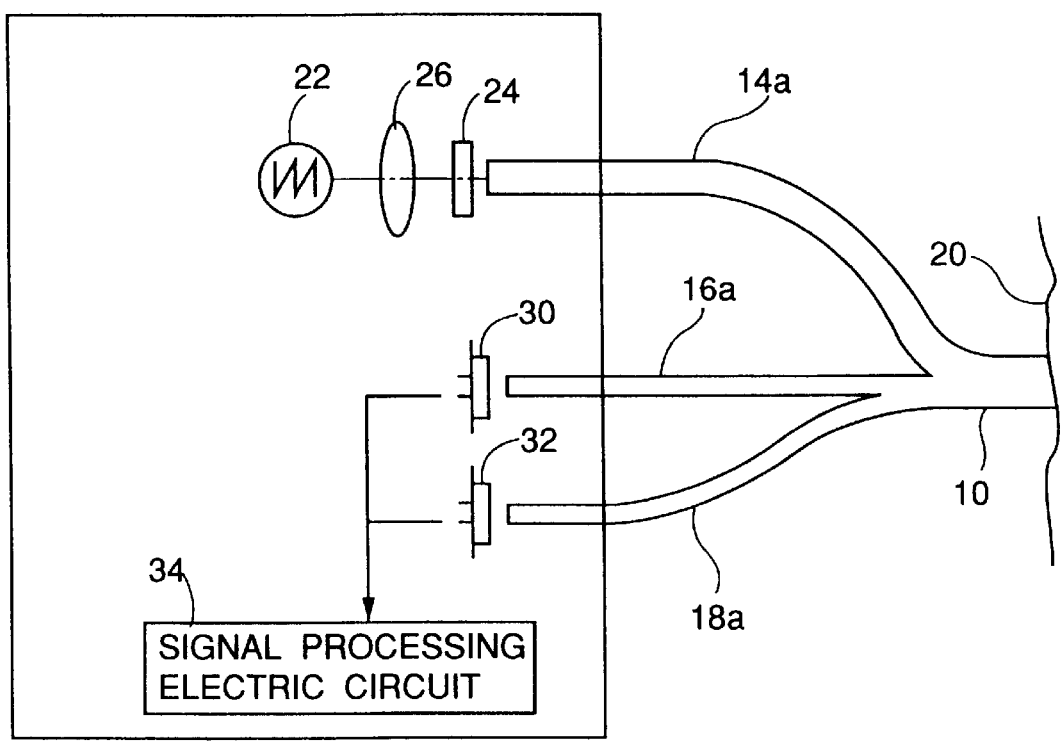

OPTICAL MEASURING APPARATUS FOR LIGHT SCATTERING

BACKGROUND OF THE INVENTION

The present invention relates to an apparatus for measuring a physical property value in a scatterer with light. The target scatterer is powder, an opaque solution such as blood or cow's milk, food such as fruit, or a human body. The powder could include raw material for medicine or for processed food such as cornstarch or flour, or industrial processing raw material such as ceramic. The physical property value to be measured is moisture content or component concentration such as protein concentration.

A method of measuring a physical property value in a scatterer is by irradiating the target substance with light through its surface and receiving the light scattered in and reflected by the target substance on another point of the surface of the target substance, thereby measuring the physical property value on the basis of data of the received light. For example, an apparatus comprising a light projecting end for projecting light on a target, a first photoreceiving end for receiving scattered/reflected light in the vicinity of the light projecting end, and a second photoreceiving end for receiving the scattered/reflected light on a position separated from the light projecting end for measuring a physical property value in a deep portion of the target has been proposed (refer to Japanese Patent Publication No. 61-11614 (1986)).

In order to improve measuring accuracy, measurement in a blank state with no object of measurement is carried out in case of a transmitter, while a reference scattering sample is employed for measuring a reference spectrum in case of a scatterer. In case of the aforementioned prior art, a signal obtained by a fiber member shown in FIG. 14 of the reference corresponds to the reference spectrum.

Further, measurement is made at two or three wavelengths for obtaining ratios of data measured at different wavelengths, thereby improving measuring accuracy.

However, the apparatus of the aforementioned prior art has the following problems:

It refers to that measurement at a deep portion as necessary for intracerebral measurement, and the distance between the light projecting end and the second photoreceiving end must be at least 4.25 cm. If the light projecting end and the second photoreceiving end are separated from each other, however, the substantial optical path length is increased, the quantity of light reaching the second photoreceiving end is extremely reduced due to absorbance or scattering in a target, and the measuring accuracy is reduced.

While a fiber bundle structure is shown in FIG. 15 of the prior art reference, a fiber member which is the second photoreceiving end is separated from the light projecting end and hence the first and second photoreceiving ends cannot be brought into identical bundle structures along with the light projecting end.

Further, in the prior art reference, a fiber member serving as the light projecting end and the fiber member serving as the second photoreceiving end are inclinedly mounted with respect to a surface of the target, and hence the quantity of light varies with the depth of the target.

While projected light spreads at 360 degrees in the target, the fiber member serving as the second photoreceiving end can receive the light only from a partial region, with inferior condensability.

The present invention is adapted to measure a physical property value at a shallow region from a surface of a target.

In order to efficiently receive light projected on the target on photoreceiving ends, a number of photoreceiving ends may be arranged around a light projecting end. FIG. 1 shows an end surface of such an optical fiber bundle. Plural light projecting optical fiber members 2 are arranged at the center, while first and second photoreceiving optical fiber members 3 and 4 are arranged around the same in multiple layers respectively.

When a number of photoreceiving ends are arranged around light projecting ends as shown in FIG. 1, the quantity of received light is increased for enabling optically bright measurement. However, the photoreceiving ends are present at different distances from the light projecting ends 2 in the first and second photoreceiving optical fiber members 3 and 4, and a plurality of data from portions of different depths intermix with each other to inevitably reduce measurement accuracy.

SUMMARY OF THE INVENTION

An object of the present invention is to improve measurement accuracy by increasing the quantity of received light while suppressing intermixture of a plurality of data from portions of different depths.

According to the present invention, a plurality of unit bundles are provided with each bundle including a light projecting optical fiber member which is arranged at the center on one end surface, a first photoreceiving optical fiber member group arranged around the light projecting optical fiber member substantially on the circumference of a first circle concentric with the optical fiber member and a second photoreceiving optical fiber member group arranged substantially on the circumference of a second circle which is concentric with the light projecting optical fiber member and larger in radius than the first circle. The bundles are so bundled that end surfaces thereof are flush with each other. The light projecting optical fiber members of these unit bundles are integrated with each other on the other end surfaces to be guided to a light source part. The first photoreceiving optical fiber member groups and the second photoreceiving optical fiber member groups of the respective unit bundles are bundled independently of each other to be guided to a photodetection part, so that light components guided by the first photoreceiving optical fiber member groups and the second photoreceiving optical fiber member groups are received as different signals in the photodetection part.

A plurality of unit bundles are bundled, whereby the number of optical fiber members forming the first and second photoreceiving optical fiber member groups in the unit bundles can be reduced. It is most preferable to arrange optical fiber members in single layers in the first and second photoreceiving optical fiber member groups respectively. This is most effective for suppressing intermixture of a plurality of data from portions of different depths. While data from the portions of different depths intermix with each other as the thicknesses of the first and second photoreceiving optical fiber member groups in the unit bundles are doubly or triply increased, reduction of measurement accuracy can be suppressed since it is not necessary to arrange the optical fiber members in multiple layers, dissimilarly to the single optical fiber bundle shown in FIG. 1.

Ends of the fiber members can be substantially perpendicularly brought into close contact with the target. Light from the light projecting optical fiber members is repeatedly scattered/reflected in/by the target, and spreads at 360 degrees. However, the first and second photoreceiving optical fiber member groups are concentrically arranged around the light projecting optical fiber members to encircle the same, whereby the respective unit bundles can effectively receive the light. In this case, the ends of the fiber members are substantially perpendicularly in close contact with the target while the first and second photoreceiving optical fiber member groups can be thinly arranged on substantially concentric circles respectively, whereby intermixture of data from portions of different depths can be suppressed.

The quantity of received light can be increased due to bundling of the plurality of unit bundles. While the unit bundles are bundled, light received by approximate optical fiber members has the strongest intensity, and hence light from light projecting optical fiber members of different unit bundles is relatively weak and has only small influence.

Proper optical path lengths can be obtained by making the distances between the light projecting optical fiber members and the first photoreceiving optical fiber member groups and those between the first photoreceiving optical fiber member groups and the second photoreceiving optical fiber member groups different from each other.

Further, the light projecting optical fiber members and the optical fiber members forming the first and second photoreceiving optical fiber member groups respectively can be so structured that the diameters thereof are not the same. The overall light quantity can be increased by thickening the light projecting optical fiber members, for example, while the quantity of light received by the second photoreceiving optical fiber member groups can be increased by thickening the diameters of the optical fiber members forming the second photoreceiving optical fiber member groups in which the quantity of light is reduced due to long substantial optical path lengths from light projecting points. The quantity of light received in the second photoreceiving optical fiber member groups can be increased also by increasing the number of the optical fiber members forming the second photoreceiving optical fiber member groups as compared with those forming the first photoreceiving optical fiber member groups. Thus, the present invention can be modified in various ways, in order to obtain an optimum quantity of light.

According to the present invention, a plurality of unit bundles, each including a light projecting optical fiber member arranged at the center on one end surface, a first photoreceiving optical fiber member group arranged around the light projecting optical fiber member substantially on the circumference of a first circle concentric with the optical fiber member and a second photoreceiving optical fiber member group arranged substantially on the circumference of a second circle which is concentric with the light projecting optical fiber member and larger in radius than first circle, are bundled for projecting light from the projecting optical fiber members of the respective unit bundles on a target while bundling the first photoreceiving optical fiber member groups and the second photoreceiving optical fiber member groups of the respective unit bundles independently of each other and guiding the same to a photodetection part for detection. In this manner, condensability is improved. Further, intermixture of data from portions of different depths can be suppressed as compared with the case of arranging the same number of photoreceiving optical fiber members on multiple concentric circles in a single bundle. Consequently, measuring accuracy is improved.

A miniature light source can be secondarily utilized so that the apparatus itself can be miniaturized and a problem of heat generation can be solved.

Measurement of reference light which comes into question in scatterer measurement is rendered unnecessary, errors in reference light measurement are eliminated, and accuracy is improved by obtaining specific absorbance from photoreceiving signals by the first and second photoreceiving optical fiber member groups. Due to internal standard measurement, further, external fluctuation such as difference between contact pressures or measured portions is cancelled and the accuracy is improved also in this point.

Miniaturization of the apparatus itself can be attained by employing a single interference filter as a spectroscopic part, or utilizing an LED (light emitting diode) or an LD (laser diode) radiating only light of a specific wavelength region as a light source. Further, substantially no condensing optical system is necessary, and hence miniaturization of the apparatus itself can be attained also in this point.

BRIEF DESCRIPTION OF THE DRAWINGS

The foregoing and other objects, features, aspects and advantages of the present invention will become more apparent from the following detailed description of the present invention when taken in conjunction with the accompanying drawings, wherein:

FIG. 5 is a schematic block diagram showing a first embodiment of the present invention;

DETAILED DESCRIPTION OF THE PREFERRED EMBODIMENTS

Figure 1:
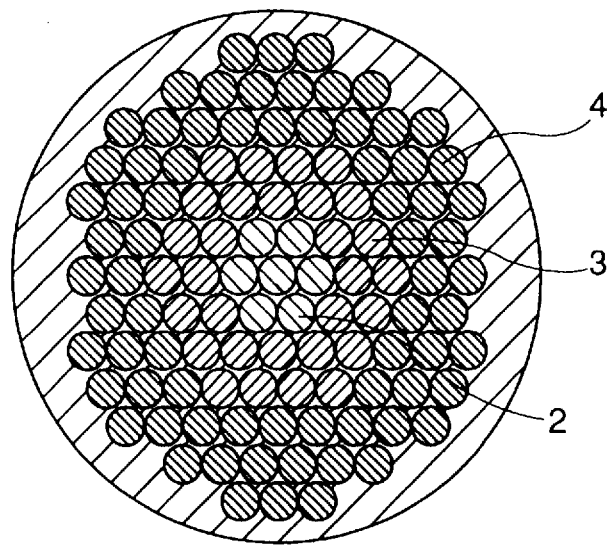
FIG. 1 is an end view showing a conventional optical fiber bundle.
Figure 2:
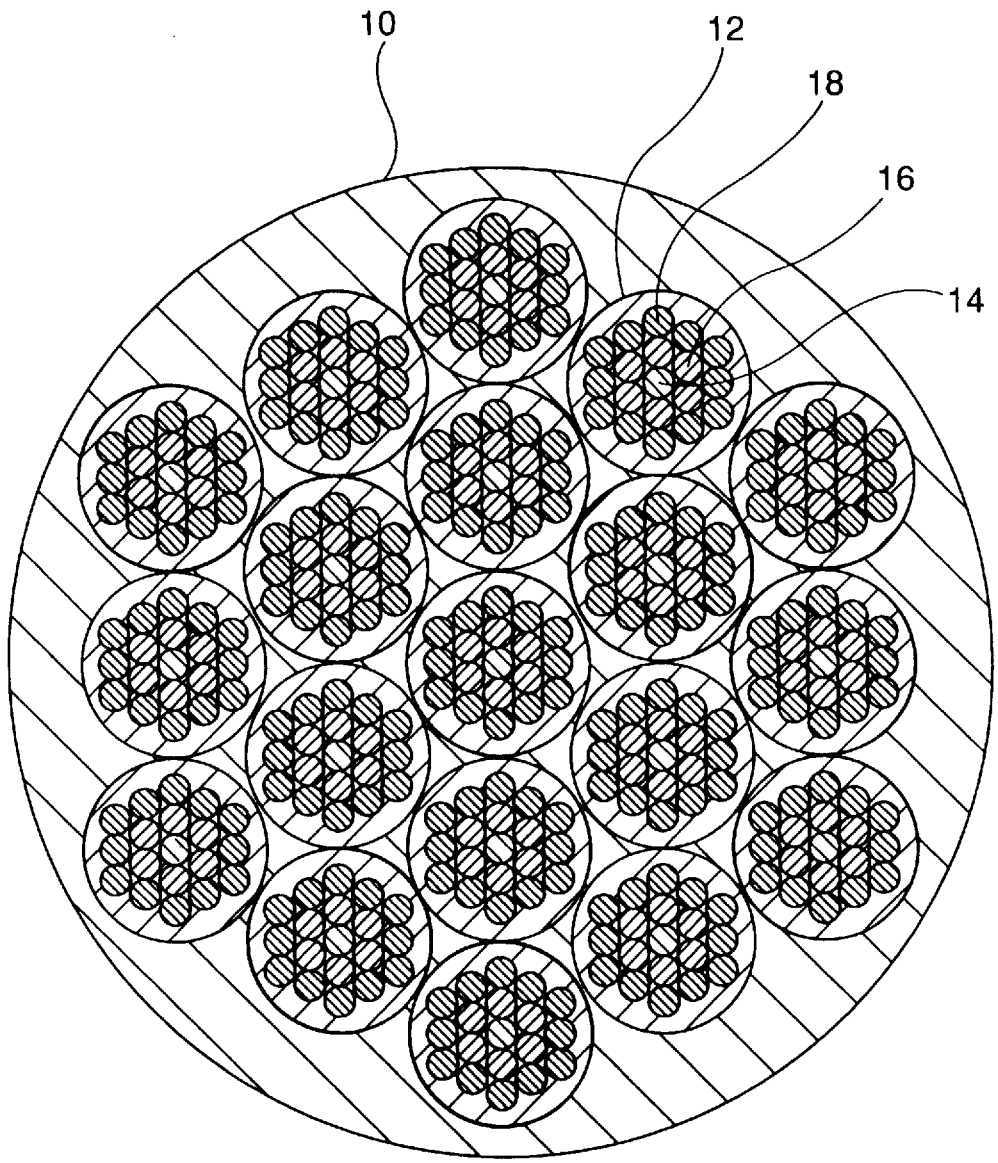
FIG. 2 is an end view showing an optical fiber bundle in a first embodiment of the present invention.

FIG. 2 illustrates an end surface, which is brought into close contact with a target, of an optical fiber light guide path 10 in an embodiment of the present invention. This optical fiber light guide path 10 is formed by bundling a plurality of unit bundles 12 so that respective end surfaces thereof are flush with each other on an end surface. The unit bundles 12 are identical in structure to each other. A light projecting optical fiber member 14 for guiding light from a light source part and projecting the same on the target is arranged at the center of each unit bundle 12. A plurality of first photoreceiving optical fiber members 16 are arranged on a substantially concentric circle around member 14, to form a first photoreceiving optical fiber member group. On a substantially concentric circle outside the first photoreceiving optical fiber member group, a plurality of second photoreceiving optical fiber members 18 are arranged to form a second photoreceiving optical fiber member group.

Figure 3A:
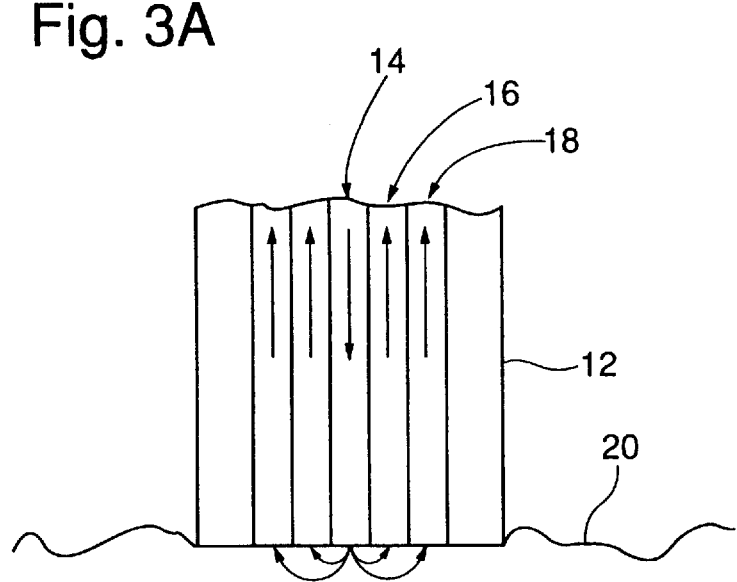
FIG. 3(A) typically illustrates optical paths in a unit bundle.
Figure 3B:
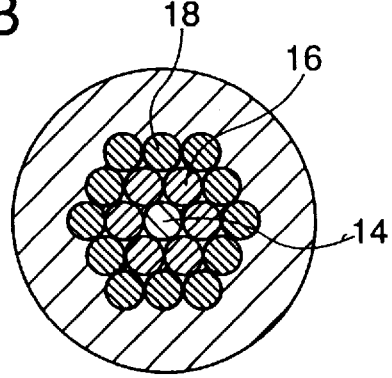
FIG. 3(B) is an end view thereof.

FIG. 3(A) typically illustrates optical paths in each unit bundle 12, and FIG. 3(B) is an end view thereof. An end surface of each unit bundle 12 is pressed against a target 20 to be in close contact therewith, and thus, all of the respective optical fiber members 14, 16 and 18 are arranged substantially perpendicularly arranged with respect to the target 20.

Light guided from the light projecting optical fiber member 14 is incident upon the target 20, scattered/reflected in the target 20 to be incident upon the photoreceiving optical fiber members 16 and 18, and guided to a detection part.

The first and second photoreceiving optical fiber members 14 and 16 are arranged in single layers respectively in this example, most preferably for suppressing intermixture of a plurality of data from portions of different depths. However, the present invention is not restricted to the first and second photoreceiving optical fibers 14 and 16 which are arranged in single layers respectively.

Figure 4A:
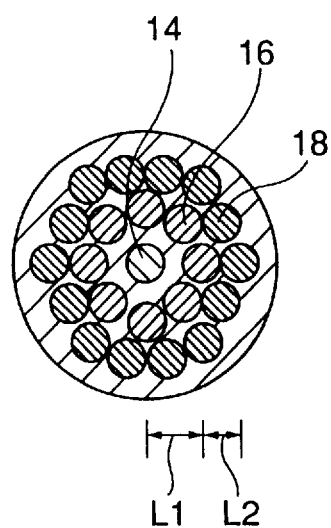
FIGS. 4(A) and 4(B) are end views showing other exemplary unit bundles employed in the present invention respectively.
Figure 4B:
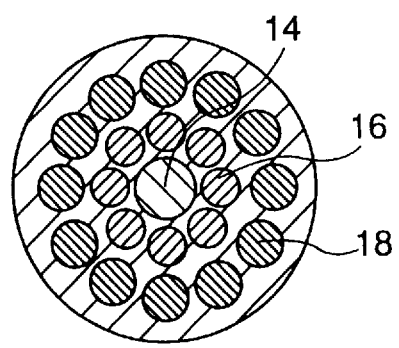

FIGS. 4(A) and 4(B) illustrate other exemplary unit bundles employed in the present invention respectively. In the example shown in FIG. 4(A), fiber members are so arranged that distances L1 and L2 between a light projecting optical fiber member 14 and first photoreceiving optical fiber members 16 and between the first photoreceiving optical fiber members 16 and second photoreceiving optical fiber members 18 are different from each other, whereby the distances between the light projecting optical fiber member 14 and the first and second photoreceiving optical fiber members 16 and 18 are optimumly set in response to a target and measuring conditions.

In the example shown in FIG. 4(B), on the other hand, diameters of optical fiber members 14, 16 and 18 are set to be different from each other. In this example, the diameters of the light projecting optical fiber member 14 and the second photoreceiving optical fiber members 18 are large, and those of the first photoreceiving optical fiber members 16 are small. The quantity of projected light can be increased by thickening the projecting optical fiber member 14, and the quantity of received light as well as a signal-to-noise ratio can be increased by thickening the second optical fiber members 18 in which the quantity of received light is reduced due to a long effective optical path length from the light projecting optical fiber member 14.

Figure 6:
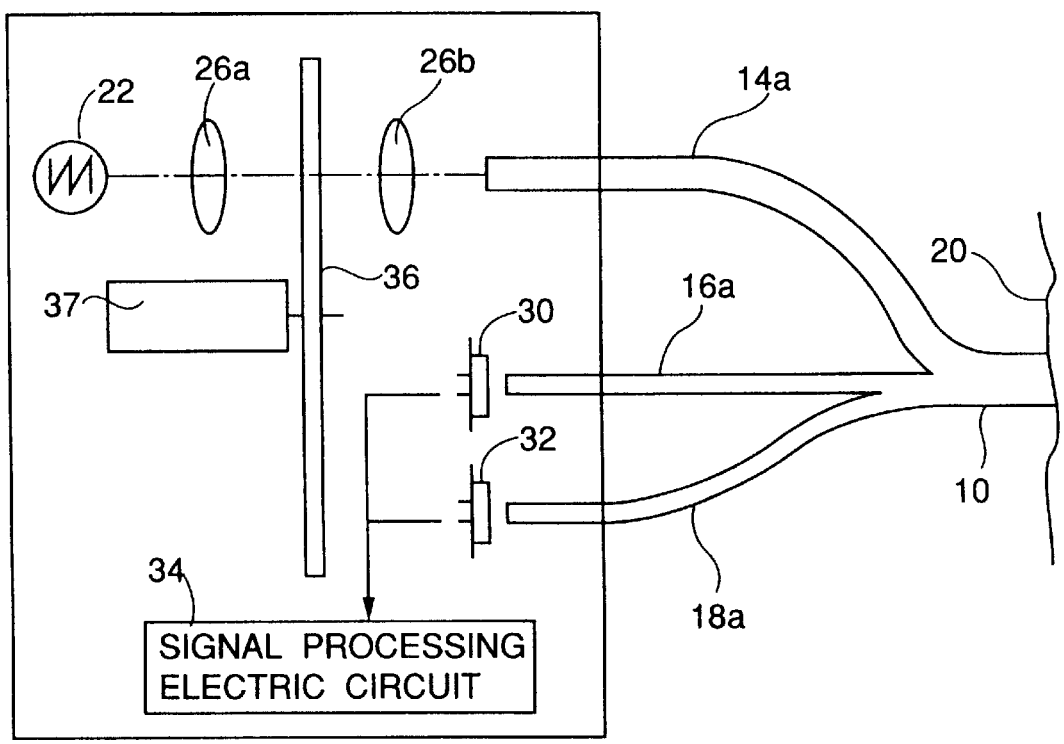
FIG. 6 is a schematic block diagram showing a second embodiment of the present invention.
Figure 7:
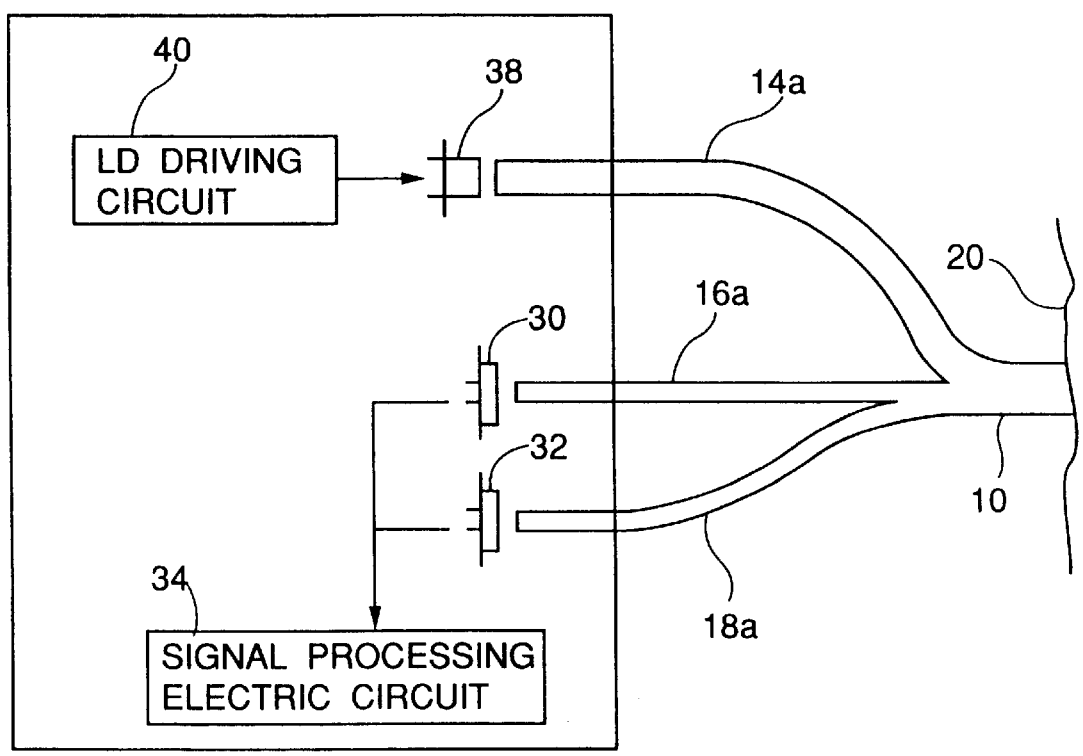
FIG. 7 is a schematic block diagram showing a third embodiment of the present invention.

FIGS. 5 to 7 schematically illustrate respective embodiments.

FIG. 5 illustrates a measuring apparatus employing a halogen lamp 22 generating light of multiple wavelengths as a light source and an interference filter 24 for selecting a specific wavelength and projecting light on a target 20. The light from the halogen lamp 22 is introduced into respective optical fiber members forming a light projecting optical fiber member group 14a through a condenser lens 26. The interference filter 24 is arranged between the condenser lens 26 and an incidence end of the light projecting optical fiber member group 14a. An optical fiber light guide path 10 has an end which is brought into close contact with the target 20 and another end which is branched into three optical fiber member groups including a light projecting optical fiber member group 14a and first and second photoreceiving optical fiber member groups 16a and 18a. The light projecting optical fiber member group 14a and the first and second photoreceiving optical fiber member groups 16a and 18a are formed by bundling the light projecting optical fiber members 14 and the first and second photoreceiving optical fiber members 16 and 18 of the respective unit bundles 12 shown in FIG. 2 respectively. Forward ends of the first and second photoreceiving optical fiber member groups 16a and 18a are guided to infrared detectors 30 and 32 respectively, for detection of the received light. A signal processing electric circuit 34 is provided as a signal processor, for fetching and processing detection signals from the infrared detectors 30 and 32.

FIG. 6 illustrates a measuring apparatus which is provided with a rotary interference filter disc 36 in place of the interference filter 24 shown in FIG. 5, so that interference filters can be switched by rotating the disc 36 by a stepping motor 37. A plurality of interference filters each having different transmission areas are arranged on the interference filter disc 36 along its circumference, so that a selected interference filter can be arranged on an optical path between a light source 22 and an incidence end of a light projecting optical fiber member group 14a. Condensing optical systems 26a and 26b, which correspond to the condenser lens 26 shown in FIG. 5 are formed by combining necessary numbers of lenses with each other.

Each of the embodiments shown in FIGS. 5 and 6 illustrates the so-called pre-spectroscopic system for selecting the wavelength before projecting the light on the target, while the so-called post-spectroscopic system of selecting a wavelength after scattering/reflecting of the light from a target may alternatively be employed.

FIG. 7 shows an example employing a laser diode (LD) 38 for generating single-wavelength light as a light source. Numeral 40 denotes a driving circuit for the laser diode 38. In this case, no filter for wavelength selection is necessary since the laser diode 38 generates single-wavelength light.

In the embodiment shown in FIG. 7, a light emitting diode (LED) may alternatively be employed as the light source.

While the infrared detectors 30 and 32 are provided for photoreceiving optical fiber member groups 16a and 18a respectively, the photoreceiving optical fiber member groups 16a and 18a may alternatively be guided to a common infrared detector through a shutter, so that the infrared detector alternately detects light from the photoreceiving optical fiber member groups 16a and 18a.

Results of actual measurement are now described. A halogen lamp of 30 W was employed as an infrared light source, an FTIR (Fourier transform infrared spectrophotometer) was employed as a spectroscopic part, and a bundle (quartz fiber member GS-180 by Sumitomo Electric Industries, Ltd.) of 117 optical fiber members each having a core diameter of 180 $\mu$m and a clad diameter of 200 $\mu$m was employed as an optical fiber light guide path 10. In this optical fiber bundle, nineteen unit bundles 12, each comprising nineteen optical fiber members including a light projecting optical fiber member 14 arranged at the center, six first photoreceiving optical fiber members 16 arranged on a substantially concentric inner circle around the periphery of the light projecting optical fiber member 14, and twelve second photoreceiving optical fiber members 18 arranged on a substantially concentric outer circle as shown in FIG. 2, were bundled for forming an optical fiber light guide path 10. PbS detectors were employed as infrared detectors 30 and 32.

Figure 8:
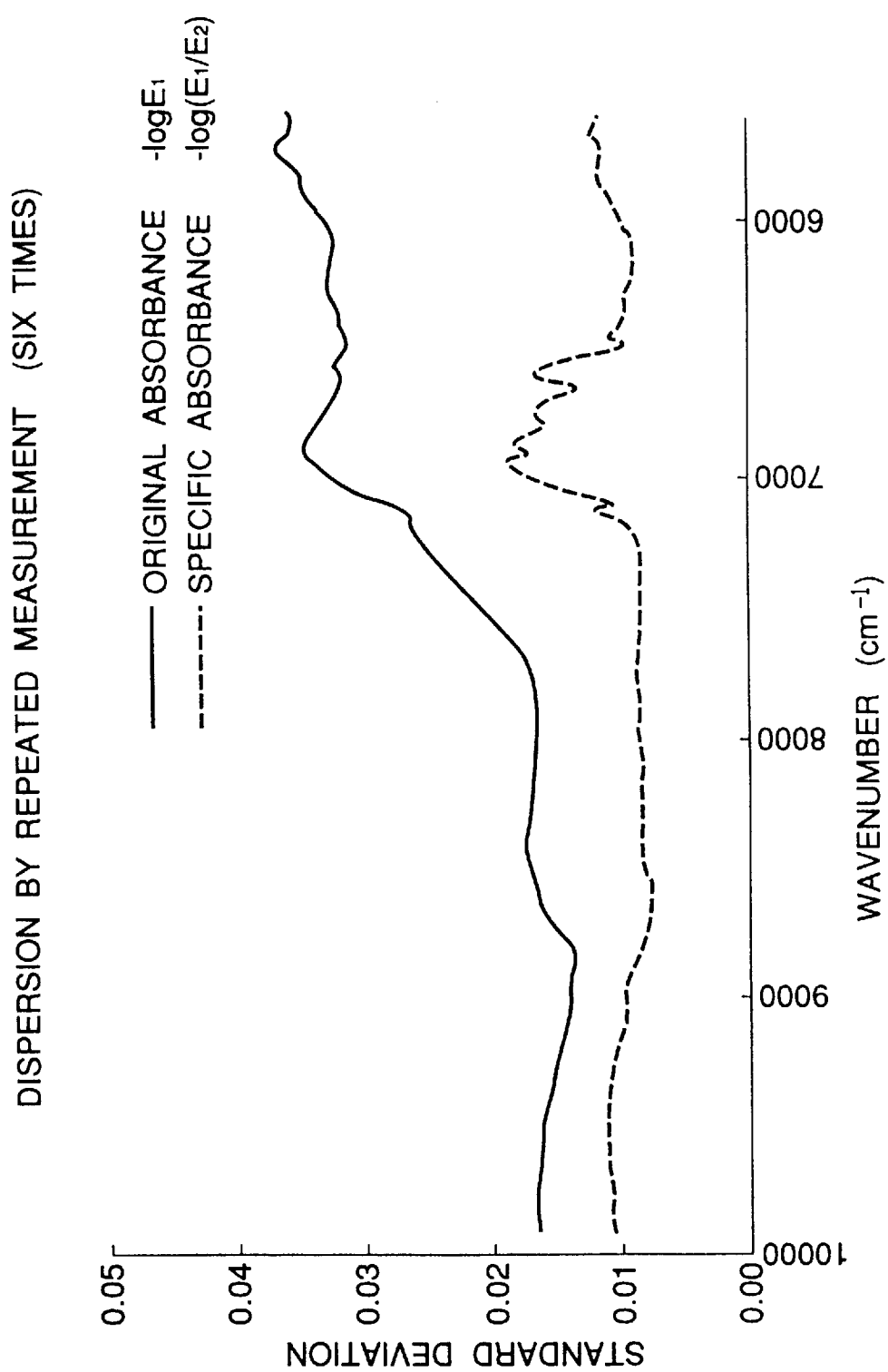
FIG. 8 illustrates standard deviations of spectra in case of repeatedly measuring human brachia in example and comparative example, respectively.

FIG. 8 shows standard deviations of spectra each obtained by bringing a base end portion of the optical fiber light guide path 10 of such a measuring apparatus into close contact with a human brachium and repeatedly measuring a near portion six times. The broken line shows specific absorbance $-\log(E_1/E_2)$, where $E_1$ and $E_2$ represent intensities of light from first and second photoreceiving optical fiber member groups respectively, and the solid line shows a result of measurement with absorbance $-\log E_1$ at a single distance from a light projecting end in comparative example. Dispersion by the repeated measurement was suppressed to 1/2 to 1/3 in the overall wavelength region due to the employment of the specific absorbance, and wavelength dependence was reduced. The dispersion is increased around 7000 to 6500 $cm^{-1}$ in FIG. 8, since infrared light was almost absorbed due to moisture absorption of the human body.

Figure 9:
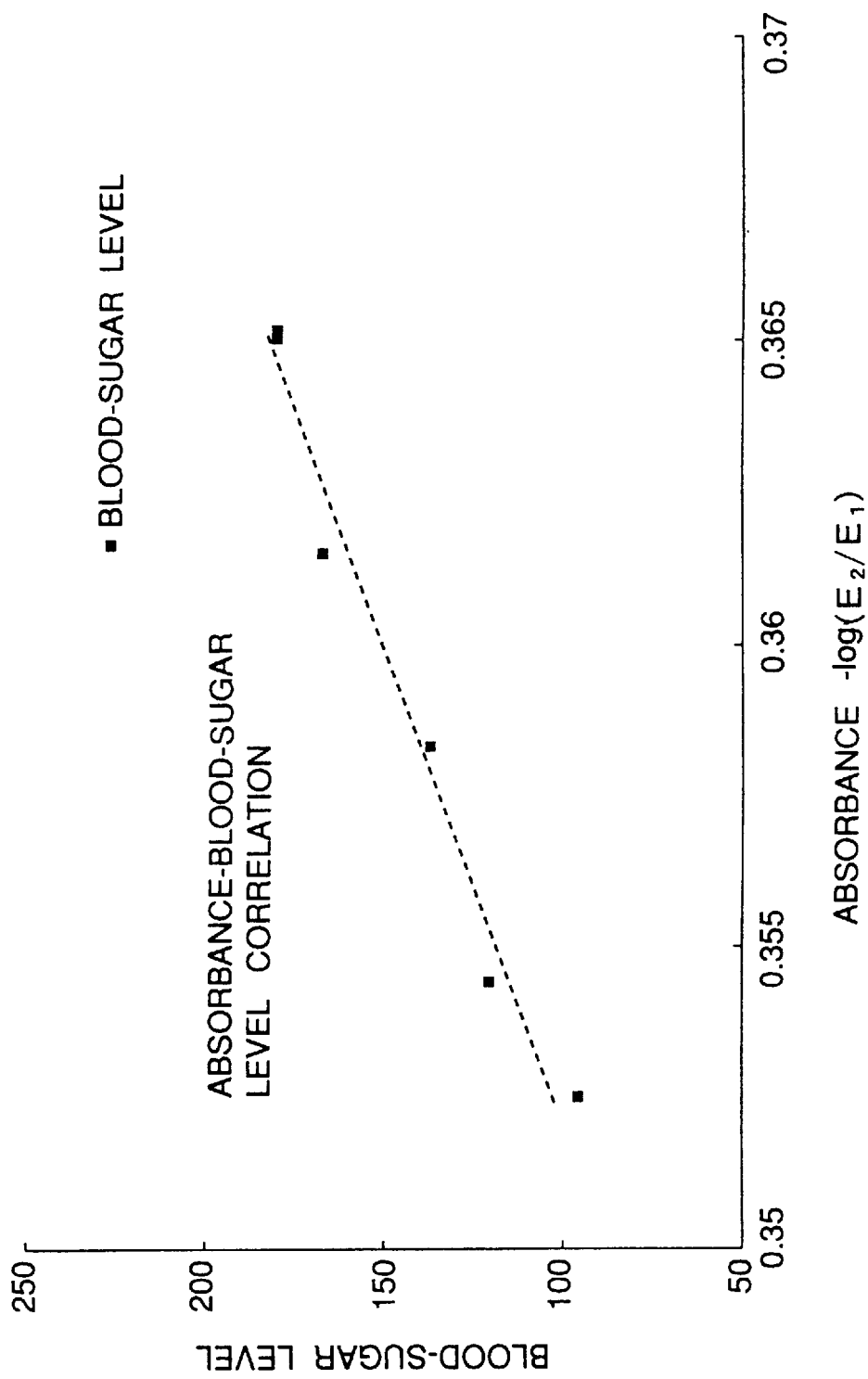
FIG. 9 illustrates correlation between blood-sugar levels in a human body and light intensities.

FIG. 9 shows exemplary correlation between blood-sugar levels in a human body and light intensities expressed in specific absorbance $-\log(E_2/E_1)$ measured by employing a silicon crystal plate as a wideband filter transmitting light of 10000 to 5400 $cm^{-1}$. Excellent correlation is observed between the blood-sugar levels and the light intensities, and it is understood that blood-sugar levels can be optically measured by employing specific absorbance.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. An optical measuring apparatus for a light scatterer comprising a light source part generating light of infrared to near infrared regions, a photodetection part comprising a photodetector having sensitivity in said infrared to near infrared regions, an optical fiber light guide path for guiding and applying said light from said light source part to a surface of a light-scattering target, receiving scattered/reflected light being generated from said surface of said target and guiding the same to said photodetection part, and a signal processor for obtaining a physical property value in said target from a detection signal of said photodetection part, wherein said optical fiber light guide path comprises a plurality of unit bundles, each unit bundle including a light projecting optical fiber member being arranged at a center on one end surface, a first photoreceiving optical fiber member group arranged around said light projecting optical fiber member substantially on the circumference of a first circle being concentric with said light projecting optical fiber member, and a second photoreceiving optical fiber member group arranged substantially on the circumference of a second circle being concentric with said light projecting optical fiber member and larger in radius than said first circle, said unit bundles being bundled with first end surfaces thereof flush with each other, said light projecting optical fiber members of respective said unit bundles being bundled and guided to said light source part on the other end surface side, and said first photoreceiving optical fiber member groups and said second photoreceiving optical fiber member groups of respective said unit bundles are bundled independently of each other and guided to said photodetection part, and said photodetection part receives respective light components guided by said first photoreceiving optical fiber member groups and said second photoreceiving optical fiber member groups as different signals.

2. The optical measuring apparatus in accordance with claim 1, wherein
said first and second photoreceiving optical fiber member groups are arranged in single layers, respectively.

3. The optical measuring apparatus in accordance with claim 1, wherein
each unit bundle has respective distances between said light projecting optical fiber member and said first photoreceiving optical fiber member group and between said first photoreceiving optical fiber member group and said second photoreceiving optical fiber member group that are different from each other.

4. The optical measuring apparatus in accordance with claim 1, wherein
diameters of said light projecting optical fiber members and optical fiber members forming said first and second photoreceiving fiber member groups are not identical.

5. The optical measuring apparatus in accordance with claim 1, wherein
the number of optical fiber members forming each said second photoreceiving optical fiber member group is larger than the number of optical fiber members forming each said first photoreceiving optical fiber member group.

6. The optical measuring apparatus in accordance with claim 1, wherein
said signal processor calculates the ratio. $E_1/E_2$ between detected intensities $E_1$ and $E_2$ of light components being guided by said first and second photoreceiving optical fiber member groups respectively in said photodetection part, or a value $-\log(E_2/E_1)$ or $-\log E_2/\log E_1$ in terms of absorbance as an optically measured value, for obtaining said physical property value of said target from a separately obtained regression formula of said optically measured value and a physical property value.

* * * * *